(12) United States Patent
Prakash (10) Patent No.: US 8,298,829 B2
(45) Date of Patent: *Oct. 30, 2012

(54) METHOD FOR IDENTIFYING THE ELUTION TIME OF AN ANALYTE

(75) Inventor: Amol Prakash, Cambridge, MA (US)

(73) Assignee: Thermo Finnigan LLC, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/013,163

(22) Filed: Jan. 25, 2011

(65) Prior Publication Data

US 2011/0114836 A1     May 19, 2011

Related U.S. Application Data

(63) Continuation of application No. 12/029,393, filed on Feb. 11, 2008, now Pat. No. 7,897,405.

(51) Int. Cl.
*B01D 59/44* (2006.01)
*B01D 59/00* (2006.01)

(52) U.S. Cl. .......... 436/161; 436/86; 250/282; 250/281; 702/19; 702/1

(58) Field of Classification Search ................. 436/161, 436/86; 702/19, 1
See application file for complete search history.

(56) References Cited

FOREIGN PATENT DOCUMENTS

WO  WO 02/052259  * 7/2002
WO  WO 2005/114930  * 12/2005

* cited by examiner

*Primary Examiner* — Christine T Mui
(74) *Attorney, Agent, or Firm* — Charles B. Katz (57) ABSTRACT

A method for determining a time of elution of a peptide of interest from a liquid chromatography column includes a step of obtaining chromatographic data for each of a plurality of candidate fragment ions of the peptide of interest. A time along a common chromatographic time is scale determined corresponding to maximum overlay of the ion signals measured for each of the plurality of candidate fragment ions. Finally, the determined time is assigned as the time of elution of the peptide of interest from the liquid chromatography column. In particular, the chromatographic data is acquired during selective reaction monitoring of an eluate from the liquid chromatography column containing the peptide of interest. The chromatographic data includes ion signals measured along the common chromatographic time scale for each of the plurality of candidate fragment ions.

7 Claims, 8 Drawing Sheets

METHOD FOR IDENTIFYING THE ELUTION TIME OF AN ANALYTE

CROSS-REFERENCE TO RELATED APPLICATIONS

The present application is a continuation under 35 U.S.C. §120 and claims the priority benefit of co-pending U.S. patent application Ser. No. 12/029,393, filed Feb. 11, 2008, which is incorporated herein by reference.

FIELD OF THE INVENTION

The instant invention relates generally to liquid chromatography/mass spectrometry (LC/MS) tandem analysis of peptides and other biomolecules, and more particularly to a method for identifying the elution time of an analyte based on its selective reaction monitoring (SRM) transitions.

BACKGROUND OF THE INVENTION

A common endpoint for biomarker discovery experiments is a list of putative marker proteins. A reasonable next step is to then perform targeted quantitative measurements of these proteins in an expanded patient population to assess their validity as markers. In one approach, selective reaction monitoring (SRM) based targeted discovery is used to filter a list of putative biomarkers down to a more targeted one. Starting with a peptide of interest, candidate fragment ions are chosen to set m/z values in the Q1/Q3 cells of a triple quadrupole mass spectrometer. As the sample flows through the liquid chromatography (LC) column, Q1/Q3 cells periodically measure signals for the m/z settings.

Unfortunately, in a complex background like plasma, various analytes can yield signals that approximate the peptide of interest, thereby leading to false positives. To quantify correctly the peptide of interest it is critical to be able to discriminate between these analytes, and identify the correct retention time of the peptide.

Accordingly, there exists a need for a method that overcomes at least some of the above-mentioned limitations.

SUMMARY OF EMBODIMENTS OF THE INVENTION

According to an aspect of the invention there is provided a method for determining a time of elution of a peptide of interest from a liquid chromatography column, comprising: providing a sample containing the peptide of interest; loading at least a portion of the sample onto the liquid chromatography column; subjecting a portion of an eluate from the liquid chromatography column containing the peptide of interest to selective reaction monitoring, comprising obtaining a chromatogram along a common chromatographic time scale for each one of a plurality of candidate fragment ions of the peptide of interest; determining a quality of overlay between the candidate fragment ions along the common chromatographic time scale; and, assigning a time along the common chromatographic time scale as the time of elution of the peptide of interest based on the determined quality of overlay between the candidate fragment ions.

According to an aspect of the invention there is provided a method for determining a time of elution of a peptide of interest from a liquid chromatography column, comprising: obtaining chromatographic data for each of a plurality of candidate fragment ions of the peptide of interest, the chromatographic data acquired during selective reaction monitoring of an eluate from the liquid chromatography column containing the peptide of interest, the chromatographic data comprising ion signals measured along a common chromatographic time scale for each of the plurality of candidate fragment ions; determining a time along the common chromatographic time scale corresponding to maximum overlay of the ion signals measured for each of the plurality of candidate fragment ions; and, assigning the determined time as the time of elution of the peptide of interest from the liquid chromatography column.

According to an aspect of the invention there is provided a computer readable storage medium having stored thereon computer-executable instructions comprising code for performing the steps of obtaining chromatographic data for each of a plurality of candidate fragment ions of the peptide of interest, the chromatographic data acquired during selective reaction monitoring of an eluate from the liquid chromatography column containing the peptide of interest, the chromatographic data comprising ion signals measured along a common chromatographic time scale for each of the plurality of candidate fragment ions; determining a time along the common chromatographic time scale corresponding to maximum overlay of the ion signals measured for each of the plurality of candidate fragment ions; and, assigning the determined time as the time of elution of the peptide of interest from the liquid chromatography column.

BRIEF DESCRIPTION OF THE DRAWINGS

Exemplary embodiments of the invention will now be described in conjunction with the following drawings, in which similar reference numerals designate similar items.

DETAILED DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
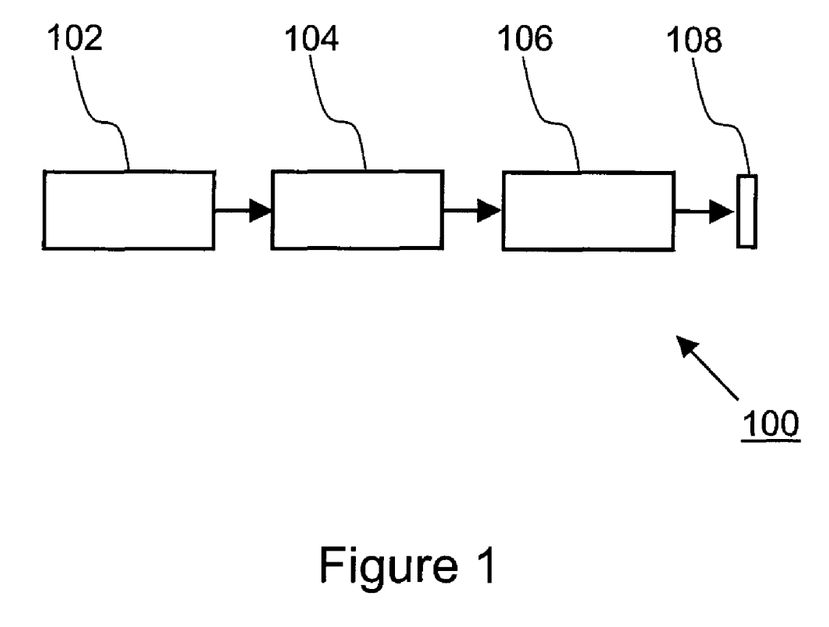
FIG. 1 is a simplified schematic diagram of a mass spectrometer system that is suitable for performing selective reaction monitoring (SRM) experiments.

Referring to FIG. 1, shown is a simplified schematic diagram of a mass spectrometer system 100 that is suitable for performing selective reaction monitoring (SRM) experiments. A SRM scan is obtained by setting a first mass separator 102 to transmit the mass of a peptide of interest to an ion fragmentor, such as for instance collision cell 104. By way of a specific and non-limiting example, the collision cell comprises a collision gas for conducting collision-induced dissociation of the peptide of interest and a quadrupole to facilitate radial confinement and transmittal of the fragment ions. Furthermore, the collision energy of collision cell 104 can be selected to facilitate producing desired fragment ions of the peptide of interest. The second mass separator 106 is set to transmit to a detector 108, ions in a mass window that is centered on the mass of a specified fragment ion so as to generate an ion signal for the fragment ion transmitted.

Suitable mass spectrometer systems include a conventional triple quadrupole mass spectrometer having two quadrupole mass filters with a collision cell disposed in the ion flight path between the two quadrupole mass filters. Other structures capable of performing the mass filtering and dissociation functions may be substituted for the quadrupole mass filters and collision cell, respectively.

A suitable ion source for the mass spectrometer system includes, but is not limited to, an electrospray ionization (ESI) or atmospheric pressure chemical ionization (APCI) source. For example, an ESI ion source supports introduction of an ionized sample that originates from a liquid chromatography (LC) column into a mass separator apparatus. One of several desirable features of ESI is that fractions of the eluate from the chromatography column can proceed directly from the column to the ESI ion source.

Figure 2:
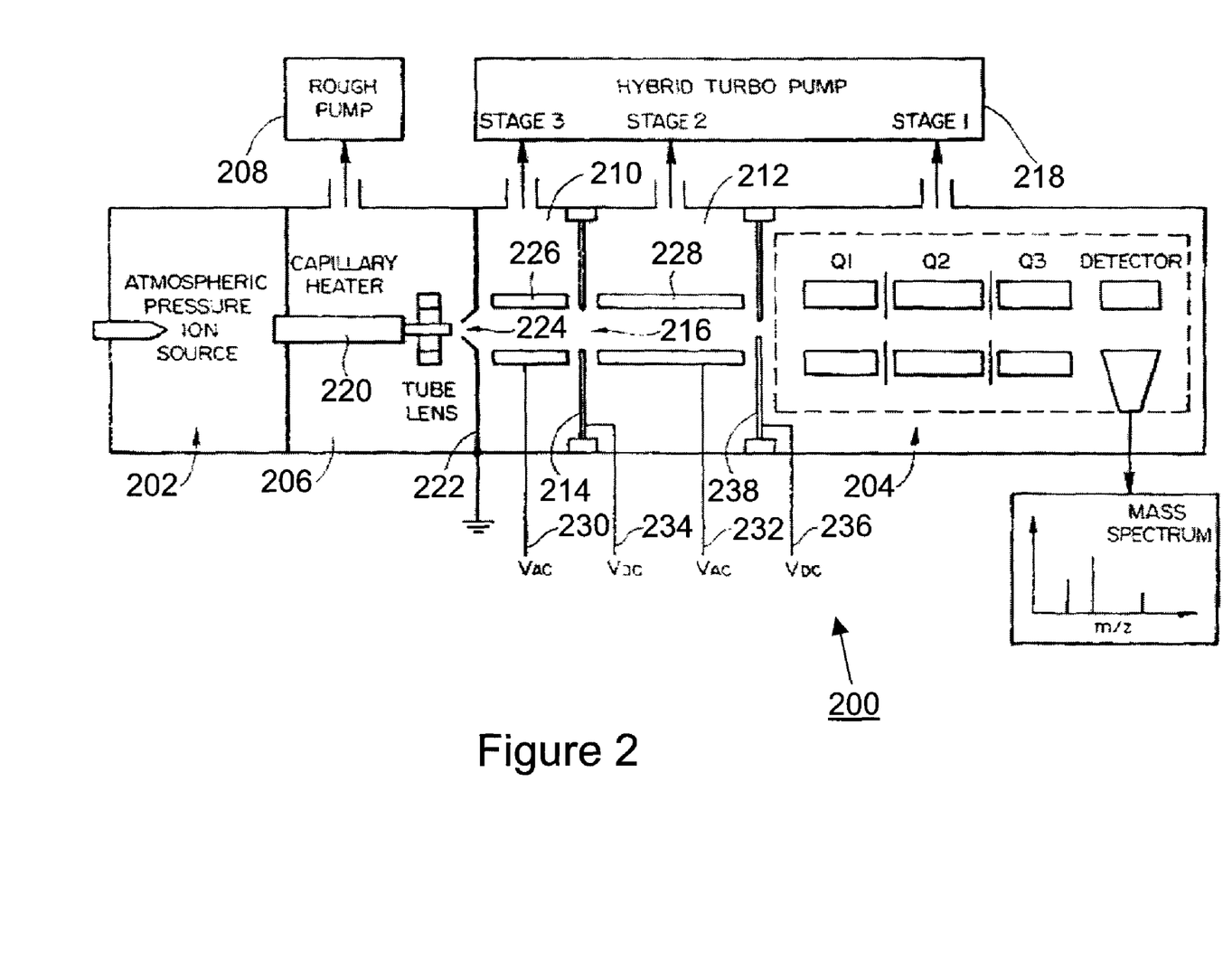
FIG. 2 is a schematic view of a triple quadrupole mass spectrometer system including an atmospheric pressure ion source coupled to a tandem mass analyzer through evacuated interface chambers with multipole ion guides.

Referring now to FIG. 2, shown is a schematic diagram of a triple quadrupole mass spectrometer system 200, which is suitable for performing SRM experiments. An atmospheric pressure ion source in chamber 202 is interfaced to a tandem mass analyzer 204 via three vacuum pumping stages. The first stage 206, which has the highest pressure, is evacuated by an oil-filled rotary vane vacuum pump 208. Other types of vacuum pumps may also be used for this stage, such as a diaphragm pump or scroll pump. The second and third stages 210 and 212 are separated by a lens 214 with an orifice 216, and can be evacuated by a hybrid or compound turbomolecular pump 218 which includes both turbomolecular and molecular drag pumping stages, and may have multiple inlets into each of these pumping stages, or by individual vacuum pumps (not shown).

The atmospheric pressure ion source may be an electrospray ion source or atmospheric pressure chemical ionization source. With either ion source, sample liquid is introduced into the chamber 202, which is at atmospheric pressure, and ionized. The ions are drawn through a capillary 220, which may be heated, into chamber 206. The end of the capillary is opposite a conical skimmer 222, which includes a central orifice or aperture 224. The skimmer separates the low pressure stage 206 from the lower pressure stage 210. A portion of the ion and gas flow is skimmed from the free jet expansion leaving the capillary and enters the second lower pressure stage. The ions that travel through the skimmer are guided into the mass analyzer by first and second multipole ion guides 226 and 228. The quadrupole ion guides are operated by applying AC voltages 230 and 232 in a prescribed phase relationship to the rod electrodes to radially confine ions in a known manner. Ions which enter the second and third stages drift under the influence of DC voltage 234 applied between the skimmer lens 222 and lens 214, by DC voltage 236 applied between the lens 214 and the lens 238, and by DC offset voltages applied to ion guides 226 and 228.

Referring still to FIG. 2, in a selective reaction monitoring (SRM) experiment a sample containing a peptide of interest is loaded onto a not illustrated liquid chromatography column, and a not illustrated pump is used to produce and deliver a solvent gradient to the column. A portion of the eluate from the liquid chromatography column is introduced into the atmospheric pressure ion source in chamber 202 to produce ions from the sample, which ions subsequently are introduced into the tandem mass analyzer 204. The Q1 of the tandem mass analyzer 204 is set (by appropriately adjusting the radio frequency and DC filtering voltages applied to the Q1 electrodes) to the m/z value of the peptide of interest, and the Q3 of the tandem mass analyzer 204 is set, sequentially in time, to the m/z value of each of a plurality of candidate fragment ion m/z values (by appropriately adjusting the radio frequency and DC filtering voltages applied to the Q3 electrodes), so as to measure the ion signal resulting for each transition corresponding to the plurality of fragment ion m/z values. A plot of the measured ion signals versus time yields a chromatogram for each of the candidate fragment ions.

According to an embodiment of the instant invention, a method is provided for scoring the quality of overlay of a plurality of candidate fragment ions in chromatographic time. In general, the candidate fragment ions are selected such that the SRM parent ion/fragment ion transitions are specific to the peptide of interest. In particular, a plurality of candidate fragment ions is selected for a particular peptide of interest. At the time the peptide of interest is eluting from the chromatographic column, each fragment ion of the plurality of candidate fragment ions is formed in the Q2 and is detected. Thus, the elution time of the peptide of interest is identified when the quality of overlay of the chromatographic peaks for each of the candidate fragment ions satisfies a predetermined criterion.

In the following discussion, M is assumed to be the m/z of the peptide of interest, and $m_{i\{i=0\ to\ N\}}$ is assumed to be the m/z of the N selected (candidate) fragment ions. Thus, the relevant Q1/Q3 settings are $M/m_1, M/m_2, \ldots M/m_N$. Furthermore, it is assumed that $X_{t\{t=0\ to\ T\}}$ is the chromatogram for these settings, where at any given time instance $X_t$ refers to the N-dimensional vector having intensities for each of the fragment ions. Let $X_{t,i}$ be the intensity observed in Q3 at time instant t and at m/z value i, and let the experimental peak width be W. Let $\overline{X_{t,i}}$ be the average of $X_{t,i}$ over the window $[t-(W/2), t+(W/2)]$. Then, the overlay quality at time s, for Q1/Q3 setting $M/m_i$ is defined as:

$$\text{Overlay}(s, M/m_i) = \frac{\sum_{t=s-\frac{W}{2}}^{t=s+\frac{W}{2}}\left[(X_{t,i} - \overline{X_{t,i}}) \times \left(\sum_{j \neq i} X_{t,j} - \sum_{j \neq i} \overline{X_{t,j}}\right)\right]}{\sqrt{\sum_{t=s-\frac{W}{2}}^{t=s+\frac{W}{2}}[X_{t,i} \times X_{t,i}] \times \sum_{t=s-\frac{W}{2}}^{t=s+\frac{W}{2}}\left[\sum_{j \neq i} X_{t,j} \times \sum_{j \neq i} X_{t,j}\right]}} \quad (1)$$

To explain Equation (1), the concept is to compute the correlation between $X_{t,i}$ and $\Sigma X_{t,j\{j \neq i\}}$, i.e., between the chromatograms for the $i^{th}$ fragment, and the sum of all fragments other than the $i^{th}$ fragment. This has the benefit of (i) maintaining independence between the variables for which the correlation is being computed, and (ii) maintaining independence over which fragment is chosen first, thus making the system free of additional parameters. Along with computing the correlation, the mean intensities of $X_{t,i}$ and $\Sigma X_{t,j}$ are also subtracted from the corresponding chromatogram in the numerator. This has the benefit of giving an "expected correlation", thus the correlation between noise patterns becomes zero.

The OverlayScore is then computed as the average of the overlays of all fragment ions, as given in Equation (2) below:

$$OverlayScore(s, M) = \frac{\sum_{i=0}^{N} Overlay(s, M/m_i)}{N} \quad (2)$$

This OverlayScore quantifies how well the various fragment ions overlay on top of each other in chromatographic time, and is useful for discriminating the peptide of interest from other analytes in a complex matrix, such as for instance plasma.

The approach for calculating an OverlayScore as described supra is presented as a specific and non-limiting example. Optionally, non-correlation based scores or scores that are not averaged over all fragment ions are calculated instead.

EXAMPLE

A specific and non-limiting example is now given in order to illustrate a method for identifying the elution time of a peptide of interest based on its SRM transitions, according to an embodiment of the instant invention. A sample containing a peptide of interest from the protein rhEPO in bovine plasma was loaded onto a C18 liquid chromatography column (15 minute gradient run), and the eluate was introduced into an atmospheric pressure ionization source coupled to a triple quadrupole mass spectrometer (TSQ Quantum Ultra). SRM scans were obtained for a plurality of precursor ion/candidate fragment ion transitions. The results of the SRM experiment are presented in FIGS. 3a and 3b, and are discussed in greater detail below.

Figure 3A:
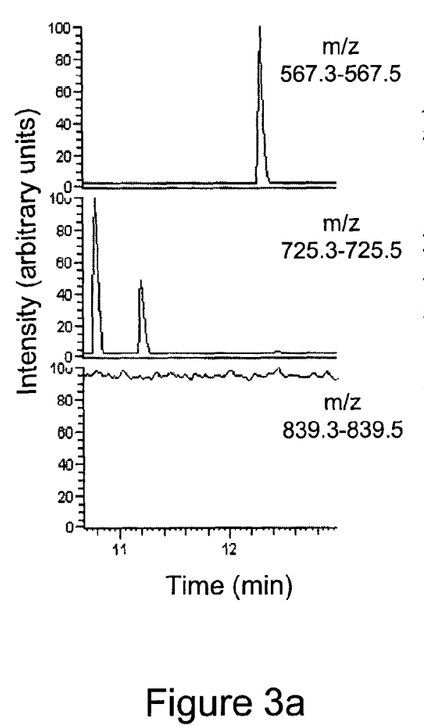
FIG. 3a shows fragment ion chromatogram traces for a false positive for a peptide of interest.

Referring now to FIG. 3a, shown are fragment ion chromatogram traces for a false positive for the peptide of interest. In particular, FIG. 3a shows the chromatogram for the Q1/Q3 settings 469.8/567.4 (top trace), 469.8/725.4 (middle trace) and 469.8/839.4 (bottom trace), during elution times between about 11 minutes and about 13 minutes. As is apparent, the bottom chromatogram trace does not contain a discernable peak for the 469.8/839.4 SRM transition, and the chromatographic peaks in the top trace and in the middle trace are not overlaid one on top of the other in chromatographic time.

Figure 3B:
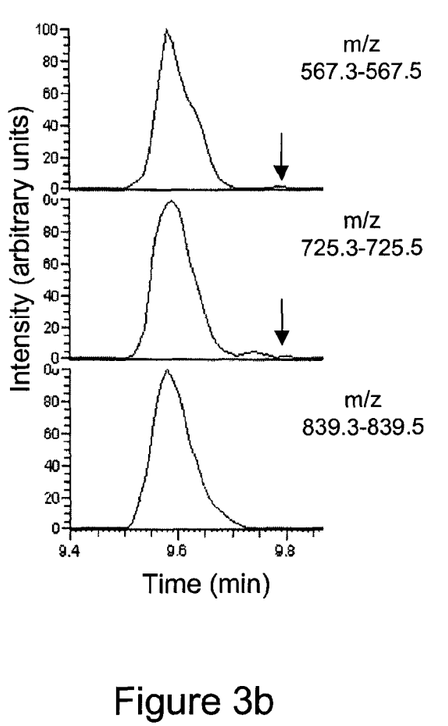
FIG. 3b shows fragment ion chromatogram traces for a true positive for a peptide of interest.

Referring now to FIG. 3b, shown are fragment ion chromatogram traces for a true positive for the peptide of interest. In particular, FIG. 3b shows the chromatogram for the Q1/Q3 settings 469.8/567.4 (top trace), 469.8/725.4 (middle trace) and 469.8/839.4 (bottom trace), during elution times between about 9.4 minutes and about 9.8 minutes. The most prominent feature in each of the three chromatograms is a peak that is centered at about 9.5 minutes. In addition, there is a lower intensity peak that appears in at least some of the chromatograms at about 9.8 minutes (as indicated in the figures by the closed headed arrow). However, the relative intensity of the ion signal is not indicative of the origin of the ions that give rise to the detected ions. Accordingly, any determination of the true elution time of the peptide of interest based on a visual observation of the chromatograms in FIG. 3b is highly subjective and prone to error.

Figure 4:
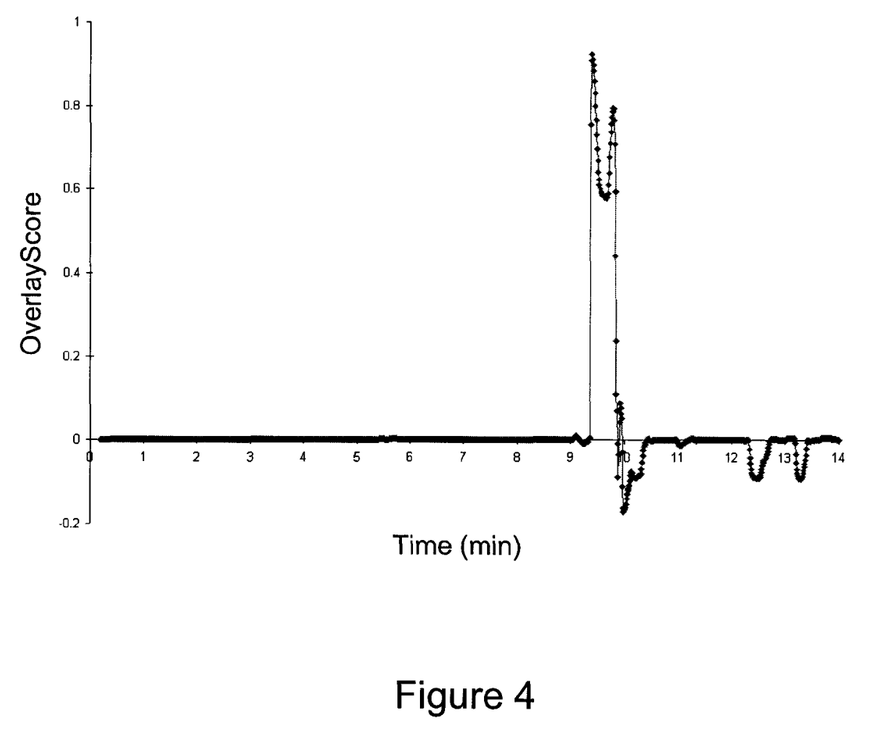
FIG. 4 is a plot showing the calculated OverlayScores versus time for particular Q1/Q3 settings.

Referring now to FIG. 4, shown is a plot of the calculated OverlayScores versus time for particular Q1/Q3 settings. The OverlayScores were determined in accordance with Equations (1) and (2), as outlined above. As is shown in FIG. 4, by using "expected correlation" the OverlayScore is zero for most of the times, but then increases rapidly at about 9.5 minutes. A second peak in FIG. 4 also appears at about 9.8 minutes, where possibly another analyte is eluting. Notably, the second peak has a lower OverlayScore (about 0.8) than does the one that is observed at 9.5 minutes (greater than about 0.9). In the instant example, the peak at about 9.5 minutes having the highest OverlayScore is attributed to elution of the peptide of interest. The second peak at about 9.8 minutes is due possibly to elution of another analyte from the LC column. Accordingly, the method successfully discriminated the analyte of interest from other analytes, thereby identifying the correct retention time of the peptide of interest. In the instant example, the OverlayScores are based on the chromatographic data relating to three candidate fragment ions. Optionally, only two candidate ions are used. Further optionally, four or more candidate ions are used.

Optionally, threshold values are determined in order to ensure that the peptides of interest are identified reliably. For instance, a suitable criterion is that an OverlayScore must exceed a predetermined minimum threshold value in order to be used in the identification of a peptide of interest. Alternatively, an OverlayScore must exceed all other OverlayScores by a predetermined minimum amount in order to be used in the identification of a peptide of interest. Of course, if similar OverlayScores are observed at plural times, then possibly the candidate fragment ions are not selective for the peptide of interest. In that case, alternate or additional candidate fragment ions are chosen, or other experimental parameters are varied.

Table 1 below presents the result of using OverlayScore on a RAW file having SRM transitions for 10 peptides from the protein rhEPO in light and heavy form. The first column gives the precursor m/z, the second column gives the various candidate fragment ions m/z, and the third column gives the retention time identified for each peptide, using the OverlayScore approach as outline supra.

| Precursor m/z | Fragment m/z | Retention Time |
| --- | --- | --- |
| 301.7 | 345.3, 432.1 | 0.9 |
| 368.7 | 460.3, 573.4 | 7.16 |
| 372.2 | 467.3, 580.4 | 7.17 |
| 402.3 | 502.3, 603.4 | 9.29 |
| 405.8 | 502.3, 603.4 | 9.29 |
| 449.7 | 636.3, 799.4 | 8.73 |
| 455.3 | 647.4, 810.4 | 8.73 |
| 462.7 | 538.3, 609.3, 710.4 | 7.82 |
| 464.3 | 567.4, 714.4, 828.4 | 9.63 |
| 469.8 | 567.4, 725.4, 839.4 | 9.61 |

Figure 5:
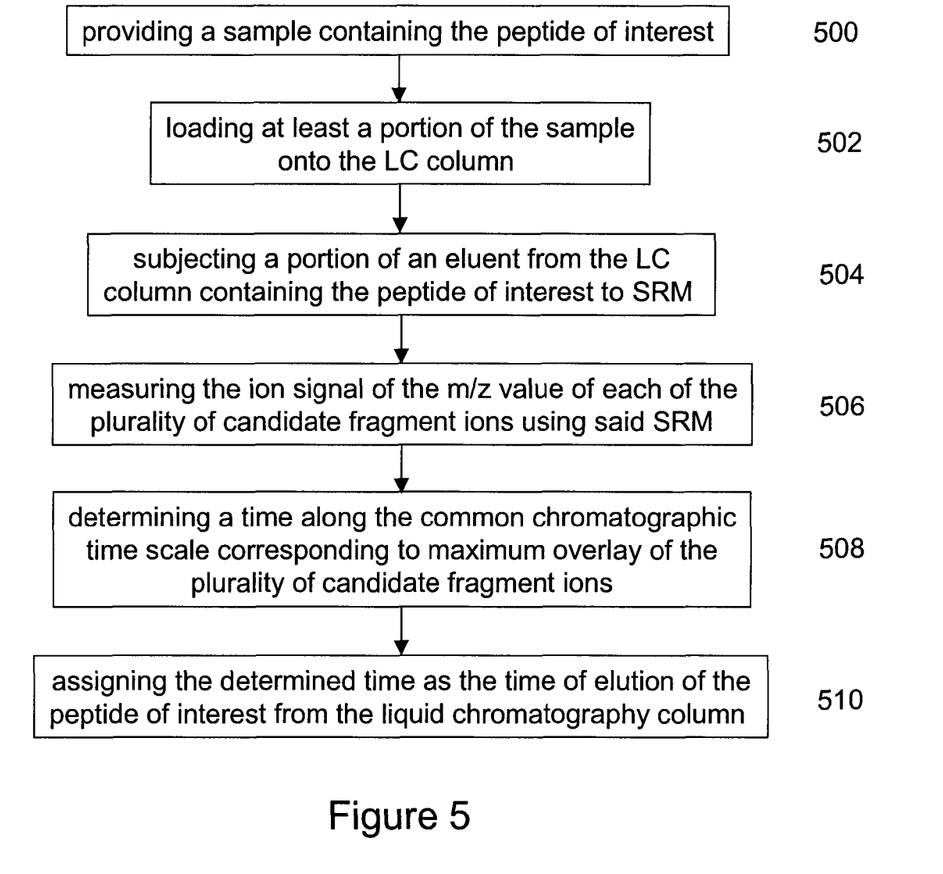
FIG. 5 is a simplified flow diagram of a method according to an embodiment of the instant invention.

Referring now to FIG. 5, shown is a simplified flow diagram of a method according to an embodiment of the instant invention. At step 500 a sample containing the peptide of interest is provided. At step 502 at least a portion of the sample is loaded onto a liquid chromatography column. At step 504 a portion of an eluate from the liquid chromatography column containing the peptide of interest is subjected to selective reaction monitoring. In particular, the transmitted parent ion m/z of each selective reaction monitoring scan is set to the m/z value of the peptide of interest and the transmitted fragment ion m/z of each selective reaction monitoring scan is set to the m/z value of a different one of the plurality of candidate fragment ion m/z values. At step 506 the ion signal of the m/z value of each of the plurality of candidate fragment ions is measured using said selective reaction monitoring, so as to obtain a chromatogram for each one of the plurality of candidate fragment ion m/z values. Each chromatogram is obtained along a common chromatographic time scale. At step 508 a time along the common chromatographic time scale corresponding to maximum overlay of the plurality of candidate fragment ions is determined. At step 510 the determined time is assigned as the time of elution of the peptide of interest from the liquid chromatography column.

Figure 6:
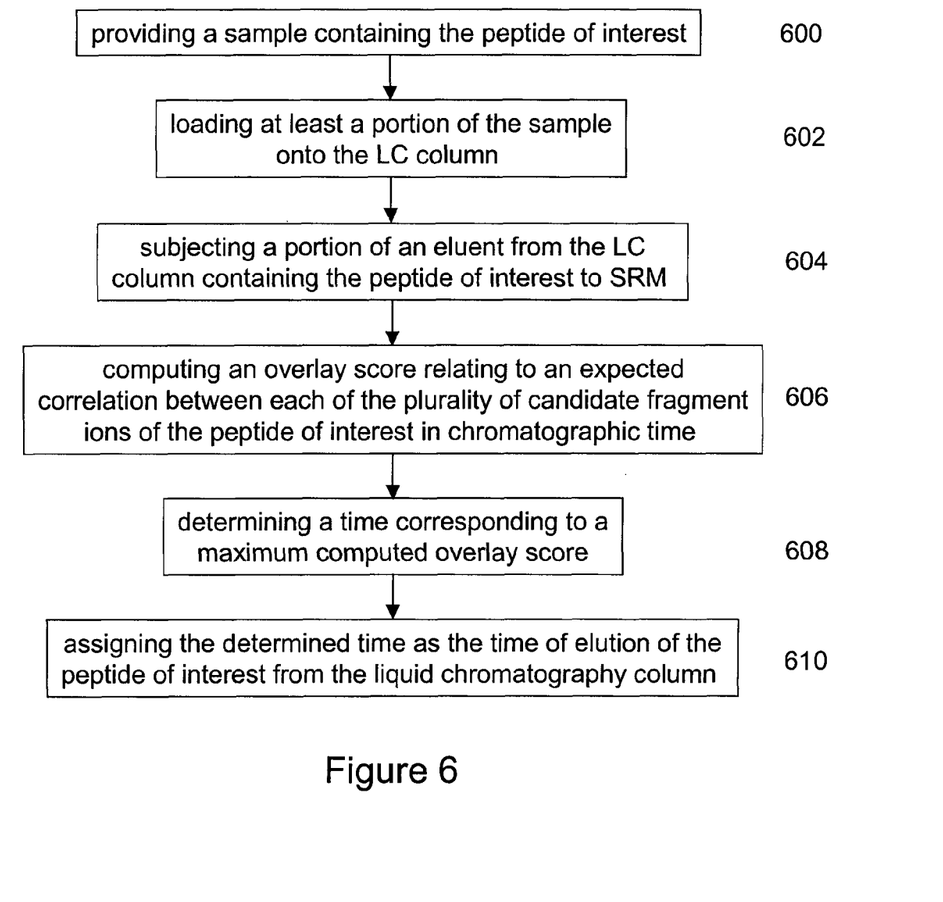
FIG. 6 is a simplified flow diagram of a method according to an embodiment of the instant invention.

Referring now to FIG. 6, shown is a simplified flow diagram of a method according to an embodiment of the instant invention. At step 600 a sample containing the peptide of interest is provided. At step 602 at least a portion of the sample is loaded onto the liquid chromatography column. At step 604 a portion of an eluate from the liquid chromatography column containing the peptide of interest is subjected to selective reaction monitoring. In particular, a chromatogram is obtained for each one of a plurality of candidate fragment ions of the peptide of interest. At step 606 an OverlayScore is computed, the OverlayScore relating to an expected correlation between each of the plurality of candidate fragment ions of the peptide of interest in chromatographic time. At step 608 a time corresponding to a maximum computed OverlayScore is determined. At step 610 the determined time is assigned as the time of elution of the peptide of interest from the liquid chromatography column.

Figure 7:
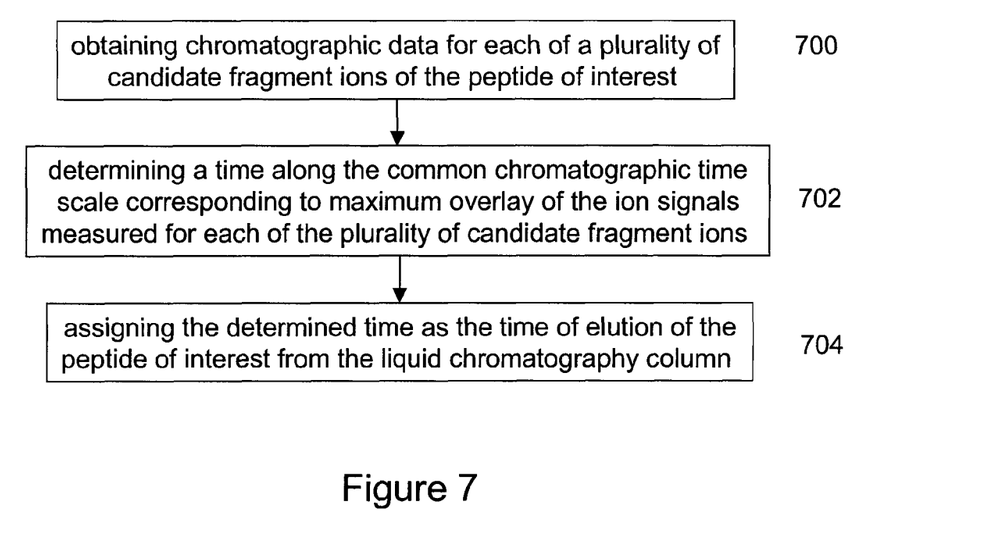
FIG. 7 is a simplified flow diagram of a method according to an embodiment of the instant invention; and, FIG. 8 is a simplified flow diagram of a method according to an embodiment of the instant invention.

Referring now to FIG. 7, shown is a simplified flow diagram of a method according to an embodiment of the instant invention. At step 700 chromatographic data is obtained for each of a plurality of candidate fragment ions of the peptide of interest. In particular, the chromatographic data is acquired during selective reaction monitoring of an eluate from the liquid chromatography column containing the peptide of interest. The chromatographic data comprises ion signals measured along a common chromatographic time scale for each of the plurality of candidate fragment ions. At step 702 a time along the common chromatographic time scale is determined corresponding to maximum overlay of the ion signals measured for each of the plurality of candidate fragment ions. At step 704 the determined time is assigned as the time of elution of the peptide of interest from the liquid chromatography column.

Figure 8:
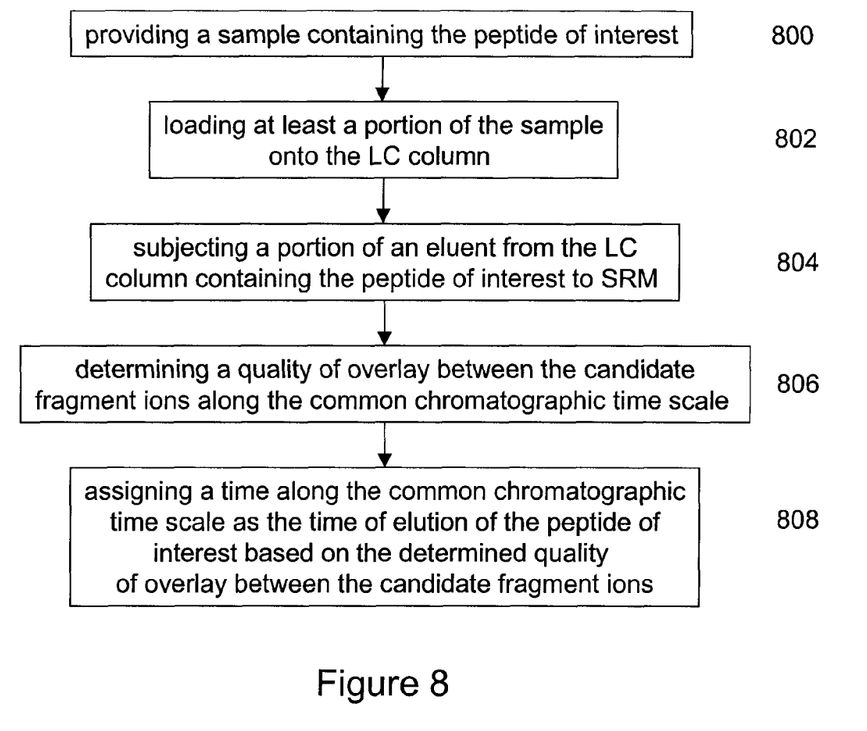

Referring now to FIG. 8, shown is a simplified flow diagram of a method according to an embodiment of the instant invention. At step 800 a sample containing the peptide of interest is provided. At step 802 at least a portion of the sample is loaded onto the liquid chromatography column. At step 804 a portion of an eluate from the liquid chromatography column containing the peptide of interest is subjected to selective reaction monitoring. In particular, a chromatogram is obtained for each one of a plurality of candidate fragment ions of the peptide of interest. At step 806 a quality of overlay is determined between the candidate fragment ions along the common chromatographic time scale. At step 808 a time along the common chromatographic time scale is assigned as the time of elution of the peptide of interest, based on the determined quality of overlay between the candidate fragment ions.

The methods described with reference to FIGS. 5 through 8 are amenable to being at least partially automated, using a suitably programmed data processing device such as for instance a personal computer based system. Thus, an embodiment of the instant invention encompasses a computer readable storage medium having stored thereon computer-executable instructions comprising code for performing at least some of the steps that are outlined above with reference to one or more of FIGS. 5 through 8. By way of a specific and non-limiting example, the computer readable storage medium has stored thereon computer-executable instructions comprising code for performing the steps of: obtaining chromatographic data along a common chromatographic time scale for each of a plurality of candidate fragment ions of the peptide of interest, determining a time along the common chromatographic time scale corresponding to maximum overlay of the ion signals measured for each of the plurality of candidate fragment ions, and assigning the determined time as the time of elution of the peptide of interest from the liquid chromatography column. For instance, the chromatographic data comprises a RAW file comprising data acquired during selective reaction monitoring of an eluate from the liquid chromatography column containing the peptide of interest. In particular, the chromatographic data comprises ion signals measured along a common chromatographic time scale for each of the plurality of candidate fragment ions.

Measuring how well the various fragment ion peaks overlay in chromatographic time provides a powerful and convenient way of discriminating the peptide of interest from other analytes. The methods according to the embodiments of the instant invention are also applicable to other large and small biomolecules, such as for instance intact proteins, metabolites, etc.

Numerous other embodiments may be envisaged without departing from the spirit and scope of the instant invention.

What is claimed is:

1. A method for verifying the detection of a substance of interest in selective reaction monitoring mass spectrometry, comprising:
    chromatographically separating a sample;
    conducting selective reaction monitoring mass spectrometry analysis of the chromatographically separated sample to monitor the variation in intensity of each of a plurality of fragment ion species formed from the substance of interest;
    computing an overlay score, the overlay score being determined from an average of overlay qualities, each overlay quality corresponding to a different one of the fragment ion species and being determined from the correlation between the intensity of the corresponding fragment ion species and the sum of intensities of the other fragment ion species at a particular timepoint in chromatographic time; and
    determining whether the substance of interest has been detected based on the computed overlay score.

2. The method of claim 1, further comprising assigning an elution time to the substance of interest, wherein the assigned elution time is a time along the chromatographic time scale for which the computed overlay score exceeds a predetermined threshold value.

3. The method of claim 2, wherein the assigned elution time is a time along the chromatographic time scale for which the computed overlay score is a maximum value.

4. The method of claim 1, wherein the substance of interest is a peptide.

5. The method of claim 1, wherein the substance of interest is a metabolite.

6. The method of claim 1, wherein the plurality of fragment ion species includes at least three fragment ion species.

7. The method of claim 1, wherein the step of conducting selective reaction monitoring mass spectrometry analysis is performed using a triple quadrupole mass spectrometer.

\* \* \* \* \*